(12) United States Patent
Matier et al.

(10) Patent No.: US 7,589,107 B2
(45) Date of Patent: *Sep. 15, 2009

(54) AMELIORATION OF VITRECTOMY-INDUCED CATARACTS

(75) Inventors: William L. Matier, Hockessin, DE (US); Ghanshyam Patil, Lincoln University, PA (US)

(73) Assignee: Othera Holding, Inc., Wilmington, DE (US)

(*) Notice: Subject to any disclaimer, the term of this patent is extended or adjusted under 35 U.S.C. 154(b) by 257 days.

This patent is subject to a terminal disclaimer.

(21) Appl. No.: 11/439,404

(22) Filed: May 22, 2006

(65) Prior Publication Data

US 2006/0292190 A1 Dec. 28, 2006

Related U.S. Application Data

(63) Continuation-in-part of application No. 10/440,583, filed on May 19, 2003, now Pat. No. 7,442,711.

(60) Provisional application No. 60/684,677, filed on May 26, 2005.

(51) Int. Cl.
*A61K 31/445* (2006.01)
*A01N 43/40* (2006.01)
*A61F 13/00* (2006.01)

(52) U.S. Cl. ................ 514/315; 514/317; 514/327; 424/422

(58) Field of Classification Search .......... 514/315
See application file for complete search history.

(56) References Cited

U.S. PATENT DOCUMENTS

| | | | |
|---|---|---|---|
| 3,936,456 A | 2/1976 | Ramey et al. ............. 544/231 |
| 4,014,335 A | 3/1977 | Arnold ..................... 424/427 |
| 4,300,557 A | 11/1981 | Refojo et al. ............. 424/424 |
| 4,404,302 A | 9/1983 | Gupta et al. .............. 524/100 |
| 4,691,015 A | 9/1987 | Behrens et al. ........... 544/198 |
| 4,871,742 A | 10/1989 | Bonne et al. |
| 4,997,652 A | 3/1991 | Wong ....................... 424/428 |
| 5,164,188 A | 11/1992 | Wong ....................... 424/428 |
| 5,378,475 A | 1/1995 | Smith et al. .............. 424/473 |
| 5,443,505 A | 8/1995 | Wong et al. ............... 623/4.1 |
| 5,462,946 A | 10/1995 | Mitchell et al. ........... 514/315 |
| 5,466,233 A | 11/1995 | Weiner et al. ............ 604/890.1 |
| 5,591,710 A | 1/1997 | Hsia ........................... 514/6 |
| 5,707,643 A | 1/1998 | Ogura et al. .............. 424/428 |
| 5,718,922 A | 2/1998 | Herrero-Vanrell et al. ... 424/501 |
| 5,725,493 A | 3/1998 | Avery et al. ................. 604/9 |
| 5,725,839 A | 3/1998 | Hsia ........................ 424/9.33 |
| 5,741,893 A | 4/1998 | Hsia ........................ 530/385 |
| 5,766,242 A | 6/1998 | Wong et al. ............... 128/498 |
| 5,767,089 A | 6/1998 | Hsia ........................... 514/21 |
| 5,773,019 A | 6/1998 | Ashton et al. ............. 424/423 |
| 5,773,021 A | 6/1998 | Gurtler et al. ............ 424/427 |
| 5,804,561 A | 9/1998 | Hsia ........................... 514/21 |
| 5,807,831 A | 9/1998 | Hsia ........................... 514/21 |
| 5,817,632 A | 10/1998 | Hsia ........................... 514/21 |
| 5,824,072 A | 10/1998 | Wong ....................... 128/898 |
| 5,824,781 A | 10/1998 | Hsia ........................ 530/385 |
| 5,840,701 A | 11/1998 | Hsia ........................... 514/21 |
| 5,869,079 A | 2/1999 | Wong et al. ............... 424/426 |
| 5,902,598 A | 5/1999 | Chen et al. ................ 424/423 |
| 5,981,548 A | 11/1999 | Paolini et al. ............. 514/316 |
| 6,001,853 A | 12/1999 | Zigler et al. .............. 514/315 |
| 6,154,671 A | 11/2000 | Parel et al. ................ 604/20 |
| 6,251,090 B1 | 6/2001 | Avery et al. ................. 604/9 |
| 6,331,313 B1 | 12/2001 | Wong et al. ............... 424/427 |
| 6,375,972 B1 | 4/2002 | Guo et al. ................. 424/423 |
| 6,410,045 B1 | 6/2002 | Schultz et al. ............ 424/429 |
| 6,429,194 B1 | 8/2002 | Leahy et al. ................ 514/8 |
| 6,433,007 B1* | 8/2002 | Garner et al. ............. 514/454 |
| 6,458,758 B1 | 10/2002 | Hsia ........................... 514/2 |
| 6,713,081 B2 | 3/2004 | Robinson et al. .......... 424/427 |
| 6,726,918 B1 | 4/2004 | Wong et al. ............... 424/422 |
| 2004/0002461 A1* | 1/2004 | Matier et al. ............. 514/18 |
| 2004/0229814 A1 | 11/2004 | Dillon ...................... 514/18 |

FOREIGN PATENT DOCUMENTS

| | | | |
|---|---|---|---|
| WO | WO 88/05044 A1 | 7/1988 |
| WO | WO 91/13619 A1 | 9/1991 |
| WO | WO03/096991 A1 | 11/2003 |
| WO | WO 2005/051328 A2 | 6/2005 |
| WO | WO 2005/055926 A2 | 6/2005 |

OTHER PUBLICATIONS

Declaration filed on Jan. 25, 2008 in U.S. Appl. No. 10/440,583.*
Ambati, J., et al., "Age-related macular degeneration: etiology, pathogenesis, and therapeutic strategies," *Survey of Ophthalmology*, 2003, 48, 257-293.
Asbell P.A., et al. "Age-related cataract," *Lancet.*, 2005, 365, 599-609.
Berra, Alejandro, et al., "Age-related antioxidant capacity of the vitreous and its possible relationship with simultaneous changes in photoreceptors, retinal pigment epithelium and Bruchs' membrane in human donors' eyes," *Arch. Gerontol. Geriatrics*, 2002, 34, 371-377.
Buerk, D.G., et al. "$O_2$ gradients and countercurrent exchange in the cat vitreous humor near retinal arterioles and venules" *Microvascular Research*, 1993, 45, 134-148.
Cejkova, J., et al., "Reactive oxygen species (ROS)-generating oxidases in the normal rabbit cornea and their involvement in the corneal damage evoked by UVB rays," *Histol. Histopathol*, 2001, 16, 523-533.

(Continued)

Primary Examiner—Jake M. Vu
(74) Attorney, Agent, or Firm—Woodcock Washburn LLP

(57) ABSTRACT

Methods to prevent, inhibit, or slow the development of vitrectomy-induced cataracts are disclosed. The methods comprise administering to the eye of a subject a composition comprising an ophthalmologically acceptable carrier or diluent and at least one hydroxylamine compound in a therapeutically sufficient amount to prevent, inhibit, or slow the development of a vitrectomy-induced cataract in the subject to which the composition is administered.

23 Claims, No Drawings

OTHER PUBLICATIONS

Chung, C.-P., et al. "Cataract formation after pars plana vitrectomy" *Kaohsiung J. Med. Sci.*, 2001, 17, 84-89.

Chylack L.T., et al., "The lens opacities classification system III. The longitudinal study of cataract study group." *Arch. Ophthalmol.*, 1993, 111, 831-836.

Chylack LT, et al. "Lens opacities classification system II (LOCSII)." *Arch. Ophthalmol*, 1989, 107, 991-997.

Hahn, S.M., et al., "In Vivo radioprotection and effects on blood pressure of the stable free radical nitroxides," *Int. J. Radiation Oncology Biol. Phys.*, 1998, 42(4), 839842.

Hahn, S.M., et al., "Evaluation of the hydroxlamine tempol-H as an in vivo radioprotector," *Free Radical Biology & Medicine*, 2000, 28(6), 953-958.

Holekamp, N.M., et al., "Vitrectomy surgery increases oxygen exposure to the lens: A possible mechanism for nuclear cataract formation." *Am. J. Ophthalmol.*, 2005, 139, 302-310.

Hsuan, J.D., et al. "Posterior subcapsular and nuclear cataract after vitrectomy" J. Cataract Refract. Surg. 2001, 27:437-444.

Kasetsuwan, N., et al., "Effect of topical ascorbic acid on free radical tissue damage and inflammatory cell influx in the cornia after excimer laser corneal surgery," *Arch Ophthalmol.*, 1999, 649-652.

Krishna, M.C., et al., "Mechanisms of hypoxic and aerobic cytotoxicity of mitomycin C in Chinese hamster V70 cells," *Cancer Res.*, 1991, 51, 6622-6628.

Mitchell, J.B., et al., "Inhibition of oxygen-dependent radiation-induced damage by the nitroxide superoxide dismutase mimic, tempol," *Archives of Biochemistry & Biophysics*, 1991, 289(1), 62-70.

Moffat, B.A., "Age-related changes in the kinetics of water transport in normal human lenses," *Exp. Eye Res.*, 1999, 69, 663-669.

Moritera, T., et al., "Microspheres of biodegradable polymers as a drug-delivery system in the vitreous" *Invest. Ophthalmol. Vis. Sci.*, 1991, 32(6), 1785-1790.

Reddan, J.R., et al., "The superoxide dismutase mimic TEMPOL protects cultured rabbit lens epithelial cells from hydrogen peroxide insult," *Exp. Eye Res.*, 1993, 56, 543-554.

Wein, F.B., et al., "Current understanding of neuroprotection in glaucoma," *Curr. Opinion in Ophthalmology*, 2002, 13, 61-67.

Zamir, E., et al., "Nitroxide stable radical suppresses autoimmune uveitis in rats," *Free Radical Biology & Medicine*, 1999, 27(1/2), 7-15.

Zhou, T, et al., "Development of a multiple-drug delivery implant for intraocular management of proliferative vitreoretinopathy" *J. Controlled Release*, 1998, 55, 281-295.

* cited by examiner

AMELIORATION OF VITRECTOMY-INDUCED CATARACTS

This application is a continuation-in-part of U.S. application Ser. No. 10/440,583, filed May 19, 2003, now U.S. Pat. No. 7,442,711 and claims benefit of U.S. Provisional Application No. 60/684,677, filed May 26, 2005. The entire contents of U.S. Provisional Application No. 60/684,677 are incorporated by reference herein.

FIELD OF THE INVENTION

The present invention is directed to methods that prevent, inhibit, or slow the development of cataracts in the eye of a subject following surgical replacement of the vitreous gel. The inventive methods comprise the administration of pharmaceutical preparations comprising hydroxylamine compounds to the vitreous cavity for treatment of the posterior side of the crystalline lens of the eye. The methods of the invention are suitable for ameliorating vitrectomy-induced nuclear, cortical, or subcapsular cataracts.

BACKGROUND OF THE INVENTION

Various publications, including patents, published applications, and scholarly or technical articles are cited throughout the specification. Each of the cited publications is incorporated by reference herein, in its entirety.

As a complex and sensitive organ of the body, the eye can experience numerous diseases and other deleterious conditions that affect its ability to function normally. Many such conditions can be found in the interior and most particularly at the rear of the eye, and affect the optic nerve and the retina, seven layers of alternating cells and processes that convert a light signal into a neural signal. Diseases and degenerative conditions of the optic nerve and retina are the leading causes of blindness throughout the world.

Cataracts are another pathology of the eye, and are characterized by a progressive opacification of the lens. The lens of the eye, located between the iris and the vitreous body, functions to focus light onto the retina. The loss of optical clarity of the lens disrupts its ability to focus light, and results in visual impairment and blindness. Cataracts are a leading cause of vision loss worldwide, and affect all demographics. Treatment of cataracts generally constitutes surgical removal of the affected lens, and replacement with an intraocular lens.

Cataracts are classified into one of three categories, based on their clinical appearance: Nuclear, which is characterized by the hardening and discoloration of the inner-most lens fibers; Cortical, which is characterized by opacification of fibers on the outside of the lens; and Subcapsular, which are opacities found primarily in the posterior portion of the lens, typically under the posterior capsule. The etiology of cataracts is not well understood, although many risk factors have been identified. Such risk factors include advanced age, genetics, gender, obesity, diabetes, and other assorted medical problems, as well as from environmental factors such as UV light, and oxygen. (Asbell P. A. et al. "Age-related cataract" *Lancet.* 2005, 365:599-609.)

Age-related cataracts result from gradual opacification of the crystalline lens of the eye. It is believed that once begun, cataract development proceeds via one or more common pathways that culminate in damage to lens fibers. This condition progresses slowly and occurs predominantly in the elderly. Alternatively, cataract may form because of surgical, radiation or drug treatment of a patient, e.g., after surgery of an eye to repair retinal damage (vitrectomy) or to reduce elevated intraocular pressure; x-irradiation of a tumor; or steroid drug treatment.

Increasing evidence indicates that an oxygen gradient is maintained within the vitreous humor of the eye, with the lowest amount of oxygen nearest to the lens, and the highest amount nearest to the retina. (Buerk, D. G. et al. "$O_2$ gradients and countercurrent exchange in the cat vitreous humor near retinal arterioles and venules" *Invest. Ophthalmol. Vis. Sci.* 1993, 41:3061-3073; and Barbazetto I. A. et al. "Oxygen tension in the rabbit lens and vitreous before and after vitrectomy" *Exp. Eye Res.* 2004, 78:917-924). Disruptions in this oxygen gradient have been proposed to contribute to cataract formation. (Holekamp, N. M. et al. "Vitrectomy surgery increases oxygen exposure to the lens: A possible mechanism for nuclear cataract formation." *Am. J. Ophthalmol.* 2005, 139:302-310).

The mechanisms by which the oxygen gradient in the vitreous humor is maintained are not well understood, although the vitreous gel apparently plays a crucial role. (Holekamp, N. M. 2005) It stands to reason that removal of the vitreous gel, as occurs in vitrectomy procedures, results in the disruption of this natural oxygen gradient.

Vitrectomies are typically indicated for, among other things, repairs to the retina, as in the case of the retinal pathologies listed above, retinal tears, or retinal detachment, for removal of blood from the vitreous humor, for the repair of macular holes, for the repair of eye trauma or for the removal of foreign objects, and for clearing vitreous infections. The vitrectomy procedure involves removal of the vitreous gel of the eye, and replacement of the vitreous gel with a balanced salt solution, air, a gas such as $SF_6$, a fluorocarbon, or a silicon oil to maintain eye pressure and shape. Following the vitrectomy, the body gradually replenishes the vitreous gel.

The vitrectomy disrupts the oxygen gradient in at least two ways. First, the surgical incisions allow oxygenated air to penetrate the vitreous cavity, and the air perfusion is further facilitated by the insertion of the surgical instruments into the eye. Second, the solution used to temporarily replace the vitreous gel contains oxygen levels much higher than the vitreous gel, and the oxygen is evenly distributed throughout the solution. (Barbazetto, I. A. 2004). As a consequence of the disruption of the oxygen gradient, the lens is exposed to levels of oxygen determined to be 2-3 times higher than normal. (Barbazetto I. A., 2004) Moreover such high levels of oxygen persist in the vitreous cavity at least 10 months following surgery. (Holekamp, N. M. 2005).

Exposure of the lens to oxygen plays a role in the formation of cataracts. Furthermore, it has been demonstrated that cataracts frequently form in patients following a vitrectomy procedure, especially if the patient is over 50. (Chung, C. P., et al. "Cataract formation after pars plana vitrectomy" *Kaohsiung J. Med. Sci.* 2001, 17:84-89; and Hsuan, J. D., et al. "Posterior subcapsular and nuclear cataract after vitrectomy" *J. Cataract Refract. Surg.* 2001, 27:437-444). Thus, a significant advancement in vitrectomy procedures would be to have available a pharmaceutical composition to administer to the patient before, during, or after the vitrectomy in order to minimize the risk of developing a cataract following the surgery by diminishing or preventing oxidative stress caused by the disruption of the natural oxygen gradient.

In addition to its role in the development of cataracts, oxidative stress has been implicated in the development or acceleration of numerous ocular diseases or disorders, including AMD and various other retinopathies. (see, e.g., Ambati et al., 2003, Survey of Ophthalmology 48: 257-293; Berra et al., 2002, Arch. Gerontol. Geriatrics 34: 371-377), as well as uveitis (e.g., Zamir et al., 1999, Free Rad. Biol. Med. 27: 7-15), glaucoma (e.g., Babizhayev & Bunin, 2002, Curr. Op. Ophthalmol. 13: 61-67), corneal and conjuctival inflammations, various corneal dystrophies, post-surgical or UV-associated corneal damage (e.g., Cejkova et al., 2001, Histol. Histopathol. 16: 523-533; Kasetsuwan et al., 1999, Arch. Ophthalmol. 117: 649-652), and presbyopia (Moffat et al., 1999, Exp. Eye Res. 69: 663-669). For this reason, agents with anti-oxidative properties have been investigated as potential therapeutic agents for the treatment of such disorders. Many investigations have focused on the biochemical pathways that generate reducing power in cells, for example, glutathione synthesis and cycling. Enzymes, such as superoxide dismutase, that reduce activated oxygen species have also been studied to determine whether they diminish cellular oxidative stress. Compounds for inhibiting lipid oxidation in cell membranes by direct radical scavenging have also been considered to be promising therapeutic interventions.

Nitroxides are stable free radicals that are reducible to their corresponding hydroxylamines. These compounds are of interest because of their radical scavenging properties, mimicking the activity of superoxide dismutase and exerting an anti-inflammatory effect in various animal models of oxidative damage and inflammation. Nilsson et al. disclosed, in WO 88/05044, that nitroxides and their corresponding hydroxylamines are useful in prophylaxis and treatment of ischemic cell damage. Paolini et al. (U.S. Pat. No. 5,981,548) disclosed N-hydroxylpiperidine compounds and their potential general utility in the treatment of pathologies arising from oxygen radicals and as foodstuff and cosmetic additives. Hsia et al. (U.S. Pat. Nos. 6,458,758, 5,840,701, 5,824,781, 5,817,632, 5,807,831, 5,804,561, 5,767,089, 5,741,893, 5,725,839 and 5,591,710) disclosed the use of stable nitroxides and hydroxylamines (e.g., tempol and its hydroxylamine counterpart, tempol-H), in combination with a variety of biocompatible macromolecules, to alleviate free radical toxicity in blood and blood components. Hahn et al. (1998, Int. J. Radiat. Oncol. Biol. Phyics 42: 839-842; 2000, Free Rad. Biol. Med. 28: 953-958) reported on the in vivo radioprotection and effects on blood pressure of the stable free radical nitroxides and certain hydroxylamine counterparts.

In ocular disorders, Zamir et al. (1999, supra) reported that the nitroxide 4-hydroxy-2,2,6,6,-tetramethylpiperidine-1-N-oxyl (TPL or tempol) reduced the severity of retinal S-antigen-induced experimental autoimmune uveoretinitis (EAU) after systemic injection in a rat model. Reddan et al. (1993, Exp. Eye Res. 56: 543-554) reported an investigation into the use of the nitroxide tempol to protect lens epithelial cells from hydrogen peroxide damage in vitro. Mitchell et al. (U.S. Pat. No. 5,462,946) also disclosed use of nitroxides (such as tempol) to protect lens epithelial cells from oxidative damage. Though Mitchell et al. also reported that the corresponding hydroxylamine tempol-H afforded no such protection (Mitchell et al., 1991, Arch. Biochem. Biophys. 289: 62-70; Krishna et al., 1991, Cancer Research 51: 6622-6628), Zigler et al. (U.S. Pat. No. 6,001,853) reported to the contrary, disclosing that the hydroxylamine was a better anti-cataractogenic composition than the corresponding nitroxide.

Due to their comparative lack of toxicity, hydroxylamines are preferable to nitroxides as therapeutic agents. However, outside the highly reducing environment of the ocular lens (M. Lou, 2003, supra), there has been no report of the use of hydroxylamine compositions for the treatment against oxidative stress to the eye that occurs during a vitrectomy procedure. Accordingly, there remains a substantial, yet unmet, need for safe, clinically useful, treatments to prevent, repress, or slow the development of cataracts and other eye disorders that arise as the result of a vitrectomy procedure.

SUMMARY OF THE INVENTION

In one aspect, the invention provides a method for inhibiting the development of a vitrectomy-induced cataract comprising administering to the eye of a subject a composition comprising an ophthalmologically acceptable carrier or diluent and at least one hydroxylamine compound in a therapeutically sufficient amount to inhibit the development of a vitrectomy-induced cataract in the subject. In some embodiments the subject is a mammal, particularly a human.

In various embodiments, the composition may be in the form of an irrigation solution, an eye drop, eye wash, ophthalmic ointment, injection, polymeric disk or a wafer. In some embodiments of the invention, the composition is administered to achieve a drug concentration of about 0.1 µM to about 10 mM; about 1 µM to about 5 mM; about 10 µM to about 2.5 mM; about 50 µM to about 1 mM; or about 1 µM to about 100 µM.

In some embodiments the hydroxylamine compound is tempol-H, tempo-H, or oxano-H, or a compound having the formula:

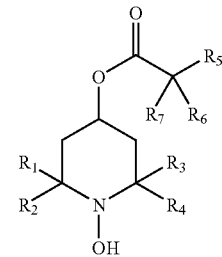

wherein $R_3$ and $R_4$ are, independently $C_1$ to $C_3$ alkyl; and where $R_1$ and $R_2$, taken together, or $R_3$ and $R_4$, taken together, or both may be cycloalkyl;

$R_5$ is H, OH, or $C_1$ to $C_6$ alkyl;

$R_6$ is $C_1$ to $C_6$ alkyl, alkenyl, alkynyl, or substituted alkyl or alkenyl;

$R_7$ is $C_1$ to $C_6$ alkyl, alkenyl, alkynyl, substituted alkyl, alkenyl, cycloalkyl, or heterocycle or where $R_6$ and $R_7$, or $R_5$, $R_6$ and $R_7$, taken together, form a carbocycle or heterocycle having from 3 to 7 atoms in the ring. In a particular embodiment, the hydroxylamine compound is 1-hydroxy-4-cyclopropanecarbonyloxy-2,2,6,6-tetramethylpiperidine hydrochloride.

In some embodiments, the method may further comprise the administration of a reducing agent. The reducing agent may be incorporated into the composition itself or be administered separately. The reducing agent may be administered before, after or simultaneously with the hydroxylamine compound. Reducing agents suitable for use include, but are not limited to sulfhydryl compound (e.g., mercaptopropionyl glycine, N-acetyl cysteine, β-mercaptoethylamine and glutathione).

In the method of the invention, the composition may be administered before vitrectomy, during vitrectomy, or after vitrectomy, and is suitable for inhibiting nuclear, cortical, and subcapsular cataracts that result from vitrectomy. In particular embodiments, a hydroxylamine composition of one formulation may be administered during vitrectomy, while the same or a different formulation may be administered before or after vitrectomy. For example, a composition may be administered by irrigation during the procedure, and additionally by intravitreal injection or topical application before or after the procedure.

Other features and advantages of the invention will be understood by reference to the detailed description and examples that follow.

DETAILED DESCRIPTION OF ILLUSTRATIVE EMBODIMENTS

Various terms relating to the methods and other aspects of the present invention are used throughout the specification and claims. Such terms are intended to be construed according to their ordinary meaning in the art. Other specifically-defined terms are to be construed in a manner consistent with the definition provided herein.

The term "vitreous" refers to the interior of the eyeball posterior to the lens. This term encompasses the vitreous tissues and network, as well as the vitreous humor. When referring to administration of compositions to the "vitreous," it is understood that a vitrectomy may entail removing all of the vitreous humor, and the composition is added to the portion of the eye previously occupied by the vitreous humor.

The term "vitrectomy" refers to the surgical removal of all or part of the vitreous humor of the eye.

The terms "vitreous humor" or "vitreous gel" are used interchangeably herein, and refer to the gelatinous fluid that fills the vitreous cavity located posterior to the lens of the eye.

The term "vitrectomy-induced cataract" refers to any opacification of the crystalline lens of the eye following a vitrectomy.

With respect to the inventive methods, the term "inhibiting the development of a vitrectomy-induced cataract" refers to any statistically significant delaying, retarding or completely preventing the opacification of the lens relative to the rate of lens opacification that would be expected in the absence of medical intervention.

The present invention provides methods for the treatment or prevention of a vitrectomy-induced cataract. The methods may be employed before, during, and/or after a vitrectomy procedure. The methods comprise administration of a composition comprising an ophthalmologically acceptable carrier or diluent and a hydroxylamine compound in a therapeutically sufficient amount to prevent, inhibit, or slow the development of a vitrectomy-induced cataract.

U.S. Pat. No. 6,001,853 to Zigler et al. ("Zigler") disclosed the use of hydroxylamines, preferably combined with reducing agents, for the inhibition of cataract development in the lens of the eye. However, the crystalline lens possesses several unique features to enable it to maintain transparency so that light can be transmitted and focused on the retina. These include (1) a high content of reduced glutathione (GSH), (2) an unusually high protein content (35-50% of its wet weight) and, significantly (3) a variety of antioxidants and oxidation defense enzymes (M. Lou, 2003, supra). The unique conditions that exist within the lens may explain why hydroxylamine compounds are found to be effective there for the prevention of cataracts. Zigler, however, did not consider the use of hydroxylamines for the prevention or inhibition of vitrectomy-induced cataract development in the lens of the eye, especially by means of treating the lens from its posterior side. Indeed, the methods disclosed in Zigler are necessarily limited in application to treatment of the anterior side of the lens. In contrast, the present inventors have determined that vitrectomy-induced cataracts also can be ameliorated or prevented through the administration of hydroxylamine compounds such as tempol-H by treatment of the lens from the posterior side.

Preferred examples of the type of hydroxylamine compounds suitable for use in the present invention are tempol-H ((the hydroxylamine reduced form of the nitroxide 4-hydroxy-2,2,6,6-tetramethylpiperidin-1-yloxy), tempo-H (the hydroxylamine reduced form of the nitroxide 2,2,6,6-tetramethylpiperidin-1-yloxy) and oxano-H (2-ethyl-2,4,4-trimethyloxazolidine, which is the reduced form of oxano, 2-ethyl-2,4,4-trimethyloxazolidin-3-yloxy). Other hydroxylamine compounds suitable for use in the present invention include, but are not limited to, those disclosed by Hahn et al. (1998, supra; 2000, supra), Samuni et al. (2001, supra); and in U.S. Pat. No. 5,981,548 to Paolini, et al. (disclosing certain N-hydroxylpiperidine esters and their use as antioxidants in a number of contexts, none ophthalmologic); U.S. Pat. No. 4,404,302 to Gupta et al. (disclosing the use of certain N-hydroxylamines as light stabilizers in plastics formulations); U.S. Pat. No. 5,462,946 to Mitchell et al. (disclosing certain nitroxides deriving from substituted oxazolidines for protection of organisms from oxidative stress); U.S. Pat. No. 3,936,456 to Ramey et al. (disclosing substituted piperazine dione oxyls and hydroxides for the stabilization of polymers); U.S. Pat. No. 4,691,015, to Behrens et al. (describing hydroxylamines derived from hindered amines and the use of certain of them for the stabilization of polyolefins); and the hydroxylamine compounds disclosed in the several aforementioned U.S. patents to Hsia et al. Most of the above-referenced compounds have not been known heretofore for administration to the eye. Certainly, none of them has been known for use in the treatment of vitrectomy-induced cataracts.

The methods of the invention may also utilize compositions comprising a pharmaceutically carrier or diluent and a hydroxylamine compound having the formula:

where $R_1$ and $R_2$ are, independently, H or $C_1$ to $C_3$ alkyl;

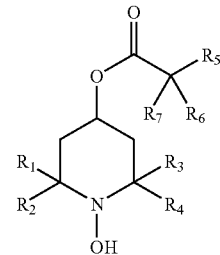

$R_3$ and $R_4$ are, independently $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is $C_1$ to $C_6$ alkyl, alkenyl, alkynyl, or substituted alkyl or alkenyl;
$R_7$ is $C_1$ to $C_6$ alkyl, alkenyl, alkynyl, substituted alkyl, alkenyl, cycloalkyl, or heterocycle or where $R_6$ and $R_7$, or $R_5$, $R_6$ and $R_7$, taken together, form a carbocycle or heterocycle having from 3 to 7 atoms in the ring. Such compounds are described in detail by Matier and Patil in WO 2003/096991 and WO 2005/055926. These compounds may also be used with ophthalmically acceptable carriers for use in ophthalmic compositions.

The methods of the present invention may also utilize compositions comprising an ophthalmically acceptable carrier or diluent and a hydroxylamine compound having an N-hydroxy piperidine portion bound to a solubility modifying portion, the compound having a solubility in water at 25° C. of at least about 0.25% by weight and a water—n-octanal partition coefficient at 25° C. of at least about 5. The composition may have the N-hydroxy piperidine portion cleavable from the compound under conditions found in the eye. It is foreseeable that this portion is cleaved under conditions in the lens of the eye. The N-hydroxy piperidine portion may be cleaved enzymatically. The compositions may also exist wherein the N-hydroxy piperidine portion is 1-oxyl-4-hydroxy-2,2,6,6-tetramethylpiperidyl.

The term $C_1$ to $C_n$ alkyl, alkenyl, or alkynyl, in the sense of this invention, means a hydrocarbyl group having from 1 to n carbon atoms in it. The term thus comprehends methyl, ethyl, n-propyl, iso-propyl, n-butyl, sec-butyl, iso-butyl, tert-butyl, and the various isomeric forms of pentyl, hexyl, and the like. Likewise, the term includes ethenyl, ethynyl, propenyl, propynyl, and similar branched and unbranched unsaturated hydrocarbon groups of up to n carbon atoms. As the context may admit, such groups may be functionalized such as with one or more hydroxy, alkoxy, alkylthio, alkylamino, dialkylamino, aryloxy, arylamino, benzyloxy, benzylamino, heterocycle, or YCO-Z, where Y is O, N, or S and Z is alkyl, cycloalkyl, heterocycle, or aryl substituent.

The term carbocycle defines cyclic structures or rings, wherein all atoms forming the ring are carbon. Exemplary of these are cyclopropyl, cyclobutyl, cyclopentyl, cyclohexyl, cycloheptyl, etc. Cyclopropyl is one preferred species. Heterocycle defines a cyclic structure where at least one atom of the ring is not carbon. Examples of this broad class include furan, dihydrofuran, tetrahydrofuran, pyran, oxazole, oxazoline, oxazolidine, imidazole and others, especially those with an oxygen atom in the ring. Five, six and seven membered rings with at least one oxygen or nitrogen atom in the ring are preferred heterocycles. Furanyl and tetrahydrofuranyl species are among those preferred.

It is preferred for certain embodiments that each of $R_1$ through $R_4$ be lower alkyl that is $C_1$ to $C_3$ alkyl. Preferably, all these groups are methyl for convenience in synthesis and due to the known efficacy of moieties having such substitution at these positions. However, other substituents may be used as well.

In certain embodiments, compounds are employed where $R_6$ is $C_1$ to $C_6$ alkyl substituted with at least one $C_1$ to $C_6$ alkoxy or benzyloxy group. Preferred among these are compounds having ethoxy or benzyloxy substituents. Among preferred compounds are those where each of $R_1$ through $R_4$ is methyl, $R_5$ is H or methyl, $R_6$ is methyl substituted with benzyloxy or $C_1$ to $C_6$ alkoxy, and $R_7$ is methyl or where $R_6$ and $R_7$ form a cyclopropyl group as well as the compound in which each of $R_1$ through $R_4$ is methyl, $R_5$ is methyl, $R_6$ is ethoxy or benzyloxy methyl, and $R_7$ is methyl. An additional preferred compound is one in which each of $R_1$ through $R_4$ is methyl, $R_5$ is methyl, $R_6$ is hydroxymethyl, and $R_7$ is methyl.

Other useful compounds are those wherein each of $R_1$ through $R_4$ is methyl, and $R_5$, $R_6$, and $R_7$ form a furanyl group, or in which $R_6$ and $R_7$ form a tetrahydrofuranyl group. The compound where $R_1$ through $R_4$ is methyl, $R_5$ is H and, $R_6$ and $R_7$ form a cyclopropyl ring is a further preferred. Examples of compounds useful in the methods of the present invention include, but are not limited to those described in U.S. Patent Publication No. US20040002461A1, and include 1-oxyl-4-(3'-ethoxy-2',2'-dimethyl)propanecarbonyloxy-2,2,6,6-tetramethylpiperidine; 1-hydroxy-4-(3'-ethoxy-2',2'-dimethyl)propanecarbonyloxy-2,2,6,6-tetramethylpiperidine hydrochloride; 1-oxyl-4-cyclopropanecarbonyloxy-2,2,6,6-tetramethylpiperidine; 1-hydroxy-4-cyclopropanecarbonyloxy-2,2,6,6-tetramethylpiperidine hydrochloride; 1-oxyl-4-(3'-benzyloxy-2',2'-dimethyl)propanecarbonyloxy-2,2,6,6-tetramethylpiperidine; 1-hydroxy-4-(3'-benzyloxy-2',2'-dimethyl)propanecarbonyloxy-2,2,6,6-tetramethylpiperidine hydrochloride; 1-hydroxy-4-(3'-hydroxy-2',2'-dimethyl)propanecarbonyloxy-2,2,6,6-tetramethylpiperidine hydrochloride; 1-oxyl-4-(1-methyl-cyclopropane)carbonyloxy-2,2,6,6-tetramethylpiperidine; 1-hydroxy-4-(1-methyl-cyclopropane)carbonyloxy-2,2,6,6-tetramethylpiperidine hydrochloride; 1-oxyl-4-(2-furan)carbonyloxy-2,2,6,6-tetramethylpiperidine; 1-hydroxy-4-(2'-furan)carbonyloxy-2,2,6,6-tetramethylpiperidine hydrochloride; 1-oxyl-4-(3'-tetrahydrofuran)carbonyloxy-2,2,6,6-tetramethylpiperidine; and 1-hydroxy-4-(3'-tetrahydrofuran)carbonyloxy-2,2,6,6-tetramethylpiperidine hydrochloride. 1-hydroxy-4-cyclopropanecarbonyloxy-2,2,6,6-tetramethylpiperidine hydrochloride is particularly preferred. This latter compound is sometimes referred to herein as "Compound 1."

The methods of the invention involve formulating one or more of the aforementioned (or other suitable) hydroxylamine compounds into compositions for application to the eye of patients in need of therapy. Thus, such compositions are adapted for pharmaceutical use as an injectable agent, or as an eye drop or in contact lenses, inserts or the like, as described in greater detail below. Accordingly, formulation of compounds into sterile water containing any desired diluents, salts, pH modifying materials and the like as are known to persons skilled in the pharmaceutical formulations art may be performed in order to achieve a solution compatible with administration to the eye. It may be that injectables, eye drops, inserts, contact lenses, gels and other liquid forms may require somewhat different formulations. All such formulations consistent with direct administration to the eye are comprehended hereby.

The compositions may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities. As such, the amount of antioxidant(s) to be administered should be enough to be effective while not causing any untoward effect. Such doses may be adjusted by a physician as needed, within the maximum levels set by regulatory authorities, and is well within the purview of the skilled artisan to determine the proper and effective dose. Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-acetylcysteine may be present in a range of about 0.1% to about 5.0% weight by volume, with about 1% to about 10% of hydroxylamine concentration being preferred. Ascorbic acid or salt may also be present in a range of about 0.1% to about 5.0% weight by volume with about 1% to about 10% weight by volume of hydroxylamine concentration preferred. Other sulfhydryls, if included, may be the same range as for N-acetylcysteine. Other exemplary compounds include mercaptopropionyl glycine, N-acetyl cysteine, β-mercaptoethylamine, glutathione and similar species, although other anti-oxidant agents suitable for ocular administration, e.g., ascorbic acid and its salts or sulfite or sodium metabisulfite may also be employed.

A buffering agent may be used to maintain the pH of any ophthalmologic compositions of the invention, for example, eye drop formulations, in the range of about 4.0 to about 8.0; so as to minimize potential irritation to the eye. In certain embodiments, the pH is maintained at about 3.5 to about 6.0, preferably about 4.0 to about 5.5, in order to ensure that most of the hydroxylamine is in its protonated form for highest aqueous solubility. The buffer may be any weak acid and its conjugate base with a pKa of about 4.0 to about 5.5; e.g., acetic acid/sodium acetate; citric acid/sodium citrate. The pKa of the hydroxylamines is about 6.0. For direct intravitreal or intraocular injection, formulations should be at pH 7.2 to 7.5, preferably at pH 7.3-7.4.

The ophthalmologic compositions may also include tonicity agents suitable for administration to the eye. Among those suitable is sodium chloride to make formulations of the present invention approximately isotonic with 0.9% saline solution.

In certain embodiments, the compositions are formulated with viscosity enhancing agents. Exemplary agents are hydroxyethylcellulose, hydroxypropylcellulose, methylcellulose, and polyvinylpyrrolidone. The viscosity agents may be present in the compounds up to about 2.0% weight by volume. It may be preferred that the agents are present in a range from about 0.2% to about 0.5% weight by volume. A preferred range for polyvinylpyrrolidone may be from about 0.1% to about 2.0% weight by volume. One skilled in the art may prefer any range established as acceptable by the Food and Drug Administration.

The compounds used in accordance with the methods of the invention may have co-solvents added if needed. Suitable cosolvents may include glycerin, polyethylene glycol (PEG), polysorbate, propylene glycol, mannitol and polyvinyl alcohol. The presence of the co-solvents may exist in a range of about 0.2% to about 4.0% weight by volume. It may be preferred that mannitol may be formulated in the compounds of the invention in a range of about 0.5% to about 4.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, and from about 0.01% to about 0.2% weight by volume of methyl or propylparabens.

Formulations for injection are preferably designed for single-use administration and do not contain preservatives. Injectable solutions should have isotonicity equivalent to 0.9% sodium chloride solution (osmolality of 290-300 mOsmoles). This may be attained by addition of sodium chloride or other co-solvents as listed above, or excipients such as buffering agents and antioxidants, as listed above. Injectable formulations are sterilized and, in one embodiment, supplied in single-use vials or ampules. In another embodiment, injectable products may be supplied as sterile, freeze-dried solids for reconstitution and subsequent injection.

The vitreous humor, exists in a highly reducing redox state, particularly nearest to the lens. It may thus be advantageous to include at least one reducing agent in the ophthalmologic compositions formulated in accordance with the invention, or to dose separately with a reducing agent to maintain the hydroxylamine in its reduced form.

Preferred reducing agents may be N-acetylcysteine, ascorbic acid or a salt form, and sodium sulfite or metabisulfite, with ascorbic acid and/or N-acetylcysteine or glutathione being particularly suitable for injectable solutions. A combination of N-acetylcysteine and sodium ascorbate may be used in various formulations. A metal chelator antioxidant, such as EDTA (ethylenediaminetetraacetic acid) or possibly DTPA (diethylenetriaminepentaacetic acid) may also be added to keep the hydroxylamine in the reduced form.

Compositions utilized in accordance with the methods of the invention may be delivered to the eye of a patient in one or more of several delivery modes known in the art. In one embodiment, the compositions are topically delivered to the eye in eye drops or washes. In another embodiment, the compositions are delivered in a topical ophthalmic ointment. In preferred embodiments, the compositions are delivered to the lens via periodic subconjunctival or intraocular injection, or by infusion in an irrigating solution such as BSS® or BSS PLUS® (Alcon USA, Fort Worth, Tex.) or by using pre-formulated solutions of the hydroxylamines in excipients such as BSS® or BSS PLUS®. Preferably, such irrigating solutions or pre-formulated solutions of hydroxylamines in excipients are used as an infusion during vitrectomy. Most preferred methods of administration will be those that provide for continuous administration to the eye, preferably into the vitreous cavity and vitreous humor such that the posterior of the lens is directly treated.

Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. A direct injection of drugs into the vitreous cavity for treating other diseases of the eye has been described, in which microspheres or liposomes were used to release drugs slowly (Moritera, T. et al. "Microspheres of biodegradable polymers as a drug-delivery system in the vitreous" *Invest. Ophthalmol. Vis. Sci.* 1991 32(6):1785-90).

In another embodiment, the composition may be delivered to or through the lens of an eye in need of treatment via a contact lens (e.g., Lidofilcon B, Bausch & Lomb CW79 or DELTACON (Deltafilcon A) or other object temporarily resident upon the surface of the eye, such as a wafer. For example, U.S. Pat. No. 6,410,045 describes a contact lens-type drug delivery device comprising a polymeric hydrogel contact lens containing drug substance in a concentration of between 0.05% and 0.25% by weight absorbed in said contact lens which is capable of being delivered into the ocular fluid.

In other embodiments, supports such as a collagen corneal shield (e.g., BIO-COR dissolvable corneal shields, Summit Technology, Watertown, Mass.) can be employed. The compositions can also be administered by infusion into the eyeball, either through a cannula from an osmotic pump (ALZET®, Alza Corp., Palo Alto, Calif.) or by implantation of timed-release capsules (OCCUSENT®) or biodegradable disks (OCULEX®, OCUSERT®) which contain the compositions. These routes of administration have the advantage of providing a continuous supply of the composition to the eye. This may be an advantage for local delivery of the hydroxylamine compounds to vitreous humor.

Several other types of delivery systems are available that are particularly suitable for delivering pharmaceutical compositions to the interior of the eye, and to the posterior of the lens. For instance, U.S. Pat. No. 6,154,671 to Parel et al. discloses a device for transferring a medicament into the eyeball by iontophoresis. The device utilizes a reservoir for holding the active agent, which contains at least one active surface electrode facing the eye tissue lying at the periphery of the cornea. The reservoir also has a return electrode in contact with the patient's partly closed eyelids. U.S. Pat. No. 5,869,079 to Wong et al. discloses combinations of hydrophilic and hydrophobic entities in a biodegradable sustained release ocular implant. In addition, U.S. Pat. No. 6,375,972 to Guo et al., U.S. Pat. No. 5,902,598 to Chen et al., U.S. Pat. No. 6,331,313 to Wong et al., U.S. Pat. No. 5,707,643 to Ogura et al., U.S. Pat. No. 5,466,233 to Weiner et al. and U.S. Pat. No. 6,251,090 to Avery et al. each describes intraocular implant devices and systems that may be used to deliver pharmaceutical compositions comprising compounds of the present invention.

Many examples of ocular implants for drug delivery are known in the art. For instance, U.S. Pat. No. 6,726,918 describes methods for treating inflammation-mediated conditions of the eye comprising: implanting into the vitreous of the eye of an individual a biodegradable implant comprising a steroidal anti-inflammatory agent and a biodegradable polymer, wherein the implant delivers the agent to the vitreous in an amount sufficient to reach a concentration equivalent to at least about 0.05 μg/ml dexamethasone within about 48 hours and maintains a concentration equivalent to at least about 0.03 μg/ml dexamethasone for at least about three weeks. Such implants are particularly suited for the methods of the present invention.

U.S. Pat. No. 6,713,081 describes ocular implant devices for the delivery of a therapeutic agent to an eye in a controlled and sustained manner. Dual mode and single mode drug delivery devices are illustrated and described. Implants suitable for subconjunctival and intravitreal placement are described. The patent also describes fabrication and implementation techniques associated with the ocular implant devices.

U.S. Pat. No. 6,429,194 describes aqueous ophthalmic preparations for instillation into the eye, or in which to pre soak or store an object to be inserted into the eye, such as a contact lens, an ointment, or a solid device to be inserted into the conjunctival sac. The ophthalmic preparation includes a mucin component, similar to that found at the normal human ocular surface.

U.S. Pat. No. 6,251,090 describes an intravitreal medicine delivery device, method and implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be controlled and allows the patient to control the timing of the delivery. The device is constructed so as to filter medicines delivered to the cavity and also avoids damage to or interference with other parts of the eye during implantation or during use.

U.S. Pat. No. 5,824,072 describes biocompatible ocular implants comprising active agents that are employed for introduction into a suprachoroidal space or an avascular region of an eye for therapeutic purposes. The administration of drugs is controlled and maintained for long periods of time, while ensuring the substantial absence of significant levels outside the site of administration.

U.S. Pat. No. 5,773,019 describes a continuous release drug delivery implant which, among other mentioned places, can be mounted either on the outer surface of the eye or within the eye. A drug core is covered by a polymer coating layer that is permeable to the low solubility agent without being release rate limiting.

U.S. Pat. No. 5,773,021 describes bioadhesive ophthalmic inserts that are placed in the conjunctival sac. The inserts are prepared by extrusion, thermoforming, or heat compression of a polymeric material matrix and the drug to be delivered. The polymeric matrix comprises a water-soluble biocompatible polymer, such as hydroxyalkyl celluloses, maltodextrins, chitosans, modified starches or polyvinyl alcohols; a water-insoluble biocompatible polymer such as an alkyl cellulose. Where applicable, a bioadhesive polymer such as polyvinyl carboxylic acid type polymers or certain bioadhesive polysaccharides or derivatives thereof may be used. The ophthalmic inserts are characterized therein as intended for the prolonged and controlled release of a medicinal substance.

U.S. Pat. Nos. 5,443,505 and 5,766,242 disclose implants comprising active agents for introduction into a suprachoroidal space or an avascular region of the eye, and describe placing microcapsules and plaques comprising hydrocortisone into the pars plana.

U.S. Pat. No. 5,378,475 describes a sustained-release implant for insertion into the vitreous of the eye. The implant has a first impermeable coating, such as ethylene vinyl acetate, surrounding most, but not all, of a drug reservoir and a second permeable coating, such as a permeable crosslinked polyvinyl alcohol, disposed over the first coating including the region where the first coating does not cover the drug reservoir, to provide a location through which the drug can diffuse out of the implant.

U.S. Pat. No. 5,725,493 describes an ocular implant device for providing drugs to the vitreous cavity over a period of time. The drug reservoir is attached to the outside of the eye with a passageway permitting medicament to enter the vitreous cavity of the eye.

U.S. Pat. No. 5,164,188 discloses encapsulated agents for introduction into the suprachoroid of the eye, and describes placing microcapsules and plaques comprising hydrocortisone into the pars plana.

U.S. Pat. No. 4,997,652 discloses biodegradable ocular implants comprising microencapsulated drugs, and describes implanting microcapsules comprising hydrocortisone succinate into the posterior segment of the eye.

U.S. Pat. No. 4,014,335 describes an ocular drug delivery device placed in the cul-de-sac between the sclera and lower eyelid for administering the drug and acting as a reservoir. The ocular device is characterized therein as administering drug to the eye in a controlled, continuous dosage rate over a prolonged time. To accomplish this, the ocular device comprises a three-layered laminate of polymeric materials holding the drug in a central reservoir region of the laminate. The drug diffuses from the reservoir through at least one of the polymeric layers of the laminate.

U.S. Pat. No. 4,300,557 teaches a capsule which can be filled with a pharmaceutical drug to be delivered which serves as an intraocular implant. The capsule is inserted in the vitreous region of the eye by making an incision in the eye, inserting the capsule and closing the incision. The capsule remains in place for a period of time and may be removed by making a second surgical incision into the eye and retrieving the device. The capsule has an attached tube which passes through the surface of the eye and extends outward from the eye useful for the subsequent injection of a drug. While in the vitreous, the device is not anchored and may move about freely.

Furthermore, Zhou et al. discloses a multiple-drug implant comprising 5-fluorouridine, triamcinolone, and human recombinant tissue plasminogen activator for intraocular management of proliferative vitreoretinopathy (PVR) (Zhou, T, et al. 1998, "Development of a multiple-drug delivery implant for intraocular management of proliferative vitreoretinopathy" *J. Controlled Release* 55:281-295).

Compositions in accordance with the methods of the invention are formulated and administered so as to apply a dosage effective for alleviating oxidative stress in the interior and posterior of the eye, and/or inhibiting the development of macular degeneration, other retinopathies or uveitis in the eye, among other utilities as discussed herein. In general, it may be preferred that the active amount be from about 0.1% to about 10.0% weight by volume in the formulation. In some embodiments, it is preferable that the active drug concentration be 0.25% to about 10.0% weight by volume. The concentration of the hydroxylamine component will preferably be in the range of about 0.1 µM to about 10 mM in the tissues and fluids. In some embodiments, the range is from 1 µm to 5 mM, in other embodiments the range is about 10 µM to 2.5 mM. In other embodiments, the range is about 50 µM to 1 mM. Most preferably the range of hydroxylamine concentration will be from 1 µM to 100 µM. The concentration of the reducing agent will be from 1 µM to 5 mM in the tissues and fluids, preferably in the range of 10 µM to 2 mM. The concentrations of the components of the composition are adjusted appropriately to the route of administration, by typical pharmacokinetic and dilution calculations, to achieve such local concentrations.

Other forms of administration, wherein the delivery to the eye is not called for, may include oral tablets, liquids and sprays; intravenous, subcutaneous and intraperitoneal injections; application to the skin as a patch or ointment; enemas, suppositories, or aerosols.

The compositions of the invention may contain more than one hydroxylamine compound. In some embodiments, the compounds of the invention are administered simultaneously. In other embodiments, the compounds of the invention are administered sequentially. The methods of the invention include combination therapy.

In some embodiments of the invention, the compound(s) of the invention are administered with another compound known in the art that is useful for treating a disease or disorder of the eye, including cataracts. Thus the methods of the invention may further comprise administering at least one other compound known in the art for treating diseases or disorders of the eye, including cataracts, and more specifically, vitrectomy-induced cataracts. The other compound(s) known in the art may be administered simultaneously with the compound(s) of the invention, or may be administered sequentially. Similarly, the methods of the invention include using such combination therapy.

For effective treatment of vitrectomy-induced cataracts, one skilled in the art may recommend a dosage schedule and dosage amount adequate for the subject being treated. It may be preferred that dosing occur one to four times daily for as long as needed. The dosing may occur less frequently if the compositions are formulated in sustained delivery vehicles, or are delivered via implant or intravitreal injection. The dosage schedule may also vary depending on the active drug concentration, which may depend on the hydroxylamine used and on the needs of the patient. For topical delivery, it may be preferred that dosing occur one to four times daily for as long as needed. The dosage amount may be one or two drops per dose. The dosage schedule may also vary depending on the active drug concentration, which may depend on the hydroxylamine used and on the needs of the patient. It may be preferred that the active amount be from about 0.1% to about 10.0% weight by volume in the formulation. In some embodiments, it is preferable that the active drug concentration be 0.25% to about 10.0% weight by volume. The concentration of the hydroxylamine component will preferably be in the range of about 0.1 µM to about 10 mM in the tissues and fluids. In some embodiments, the range is from 1 µm to 5 mM, in other embodiments the range is about 10 µM to 2.5 mM. In other embodiments, the range is about 50 µM to 1 mM. Most preferably the range of hydroxylamine concentration will be from 1 to 100 µM. The concentration of the reducing agent will be from 1 µM to 5 mM in the tissues or fluids, preferably in the range of 10 µM to 2 mM. The concentrations of the components of the composition are adjusted appropriately to the route of administration, by typical pharmacokinetic and dilution calculations, to achieve such local concentrations.

An ophthalmologist or one similarly skilled in the art will have a variety of means to monitor the effectiveness of the dosage scheme and adjust dosages accordingly. For example, effectiveness in the prevention or suppression of the development of vitrectomy-induced cataracts may be determined by observing the degree of opacity of the lens using direct observation through a slit lam or by photography of the lens. Various lens opacity grading systems, such as LOCS II or LOCS III, are commonly used to establish the severity of the opacity. In addition, cataract formation may be monitored by loss of visual acuity. (Chylack L.T. et al. "The lens opacities classification system III. The longitudinal study of cataract study group." *Arch. Ophthalmol.* (1993) 111:831-836; and Chylack L T et al. "Lens opacities classification system II (LOCSII)." *Arch. Ophthalmol,* (1989) 107:991-997). Following such evaluation, the ophthalmologist may adjust the frequency and/or concentration of the dose, if needed.

It may be preferred that at least 0.1% solubility is needed for an eye drop, even for a suspension formulation. Completely water-insoluble compounds may not be effective. Esters that are soluble in water (>0.1% weight by volume) are preferred. For certain esters with less than 0.1% solubility may be used in the form of suspensions or ointments or other formulations. Solubility is determined by mixing 100 mg of test compound with 1 ml of water, at room temperature and adding additional 1 ml quantities of water, with mixing, until ester dissolves completely.

Corneal penetration is shown by measuring a substantial concentration (e.g. >5 µM) of the effective hydroxylamine and/or ester in the aqueous humor after administering a solution of the compound in vivo to the eyes of rabbits. This is determined by electron spin resonance (ESR), high performance liquid chromatography (HPLC) or gas chromatography (GC) assay of the rabbit aqueous humor. In vitro corneal penetration methods may also be used prior to the in vivo testing method particularly for screening compounds. Penetration of compounds to the interior or posterior of the eye is likewise shown by measuring the concentration of the compound in the vitreous humor, uvea or retina after administering a solution of the compound to the eyes of rabbits.

Esters are selected for these tests based on their calculated or measured octanol/water partition coefficient (P).

Enzymatic conversion is essentially complete at greater than 90% hydrolysis of the ester in vivo to the alcohol and acid after administering the compound to the eye of rabbits. The conversion may be determined by HPLC or GC assay of a selected eye tissue (e.g., aqueous humor). Alternatively, the enzymatic conversion may be determined by incubating the compound in plasma or eye tissue homogenate and assaying samples periodically by HPLC or GC to monitor the rate of breakdown. Esters with a half-life of less than about 1 or 2 hours are preferred candidates.

Esters should have less than about 10% hydrolysis at 40° C., after 3 months, in aqueous solution at pH 4.0-5.0. This extrapolates to a shelf life of the ester in solution of at least 18 months at room temperature, which may be preferred for an eye drop product.

The methods of the invention are useful for inhibiting a vitrectomy-induced cataract, and comprise administering to the eye of a subject a composition comprising an ophthalmologically acceptable carrier or diluent and at least one hydroxylamine compound in a therapeutically sufficient amount to inhibit the development of a vitrectomy-induced cataract in the subject. The methods are suitable for inhibiting vitrectomy-induced cortical, nuclear, or subcapsular cataracts.

In one embodiment, the hydroxylamine compounds are administered to the vitreous of the subject while the subject is undergoing the vitrectomy procedure by means of the irrigation solution used to replace the vitreous humor. The hydroxylamine compounds may be coadministered with the irrigation solution or administered after the placement of the irrigation solution in the vitreous cavity. In a preferred embodiment, the hydroxylamine compounds are formulated as part of the irrigation solution. In another embodiment, the hydroxylamine compounds are administered to the subject after the vitrectomy procedure, as part of a post-vitrectomy follow-up regimen. After the vitrectomy, the hydroxylamine compounds may be administered to the vitreous of the subject by means of injection, or may be administered topically, for example, by means of an eye drop, eye wash, ophthalmic ointment, and the like as set forth herein. It is preferred that the hydroxylamine compounds administered topically can diffuse across the cornea and aqueous humor to enter the lens and vitreous. Most preferably, such compounds treat the lens from its posterior side.

In a preferred embodiment, the hydroxylamine compounds are administered to the vitreous of the subject both during the vitrectomy procedure and after the vitrectomy procedure as part of a post-vitrectomy follow-up regimen. While the subject is undergoing the vitrectomy, the hydroxylamine compounds may be coadministered with the irrigation solution, administered after the placement of the irrigation solution in the vitreous cavity, or preferably, the hydroxylamine compounds are formulated as part of the irrigation solution. After the vitrectomy, the hydroxylamine compounds may be administered to the vitreous of the subject by means of injection, or may be administered topically, for example, by means of an eye drop, eye wash, ophthalmic ointment, and the like as set forth herein. It is preferred that the hydroxylamine compounds administered topically can diffuse across the cornea and aqueous humor to enter the lens and vitreous. Most preferably, such compounds treat the lens from its posterior side. In one embodiment, the hydroxylamine compounds are administered to the vitreous of the subject by means of a combination of injection and topical administration.

In another preferred embodiment, the hydroxylamine compounds are administered to the vitreous of the subject before the vitrectomy procedure, during the vitrectomy procedure, and after the vitrectomy procedure as part of a post-vitrectomy follow-up regimen. Before the vitrectomy, the hydroxylamine compounds may be administered to the vitreous of the subject by means of injection, or may be administered topically, for example, by means of an eye drop, eye wash, ophthalmic ointment, and the like as set forth herein. It is preferred that the hydroxylamine compounds administered topically can diffuse across the cornea and aqueous humor to enter the lens and vitreous. Most preferably, such compounds treat the lens from its posterior side. While the subject is undergoing the vitrectomy, the hydroxylamine compounds may be coadministered with the irrigation solution, administered after the placement of the irrigation solution in the vitreous cavity, or preferably, the hydroxylamine compounds are formulated as part of the irrigation solution. After the vitrectomy, the hydroxylamine compounds may be administered to the vitreous of the subject by means of injection, or may be administered topically, for example, by means of an eye drop, eye wash, ophthalmic ointment, and the like as set forth herein. It is preferred that the hydroxylamine compounds administered topically can diffuse across the cornea and aqueous humor to enter the lens and vitreous. Most preferably, such compounds treat the lens from its posterior side.

The following examples are set forth to describe the invention in greater detail. They are provided merely to illustrate the invention, not to limit the scope of the invention in any way.

EXAMPLE 1

Ocular Tissue, Urine and Plasma Levels of Total Radioactivity in New Zealand White Rabbits Following a Single Intravitreal Dose of Tempol-H A randomized, single treatment study, in nine groups of three NZW rabbits per group, was conducted. Animals were assigned to study groups by a computerized randomization program designed to achieve similar body weights per group. Naïve animals received an intra-vitreous injection of the test article at a nominal dose of 2.0 mg*eq [$^{14}$C]Tempol-H (1,4-dihydroxy-2,2,6,6-tetramethylpiperidine(2,4,6-$^{14}$C$_3$)). A dose of 0.1 mL, containing 2.18 µCi was administered into both eyes. At nine specified time points post dose (1, 30, 60 minutes, 2, 4, 8, 24, 48, and 120 hours), three animals per group were euthanized and terminal samples were collected. The following tissues were harvested from each eye of all animals: aqueous humor, cornea, iris/ciliary body complex, vitreous humor, lens, retina-choroid plexus and optic nerve. Blood was collected from the marginal ear vein of all rabbits into tubes containing K$_3$EDTA; urine was cage-collected daily from three animals up to 120 hour post dosing. Total radioactivity was determined in all samples by liquid scintillation counting.

Results: Quantifiable levels of total radioactivity were observed in all sampled ocular tissues, blood and plasma. At one minute post dosing, the highest concentrations of radioactivity were found in the retina-choroid plexus, vitreous humor and iris-ciliary body complex. The radioactivity distributed rapidly from the injection site to other ocular tissues. The highest concentrations of radioactivity in vitreous humor, retina-choroid plexus, iris-ciliary body complex, optic nerve, lens, cornea and aqueous humor were observed at 0.5, 0.017, 0.017, 0.5, 2.0, 4.0, and 48 hr, respectively. Approximate concentrations of radioactivity (µg eq/g) at 8 hours post dosing in the respective ocular tissues were: 30±8 in the aqueous humor, 2±0.1 in the cornea, 6±0.5 in the iris/ciliary body, 25±3 in the vitreous humor, 41±6 in the lens, 4±0.5 in the optic nerve, and 18±2 in the retina-choroid plexus.

EXAMPLE 2

Method to Ameliorate Vitrectomy-Induced Cataract Development

The present invention provides methods to prevent, inhibit, or slow the development of a cataract during or following a surgical replacement of the vitreous gel in a subject such as a mammal, including without limitation rabbits, rats, dogs, cats, or humans. The methods comprise administering a hydroxylamine compound, or hydroxylamine compound in combination with a reducing agent, to a subject in a ophthalmologically compatible carrier, and in an amount effective to prevent, inhibit, or slow the development of vitrectomy-induced cataracts in the crystalline lens of the eye. The methods of the invention are suitable for treatment against vitrectomy-induced nuclear, cortical, or subcapsular cataracts.

The hydroxylamine compound may be administered to the vitreous cavity before, during, and after the vitrectomy procedure. In this prophetic example, the lens is pre-treated with the hydroxylamine compound by direct injection into the vitreous cavity within two weeks prior to the vitrectomy. Alternatively, the pre-treatment may be topically administered to the eye, for example, through an eye drop. In either case, the hydroxylamine compound may be administered to the subject in multiple doses, and over the course of multiple days. The proper dosage and optimal number of times to administer the compound will be empirically determined, according to methods routine in the art.

The hydroxylamine compound will be administered to the subject again during the vitrectomy procedure. During vitrectomy surgery, the vitreous humor is surgically removed, but is replaced with an aqueous irrigating solution such as BSS to maintain the pressure, shape, and contour of the eye until the body replenishes the vitreous humor. Vitrectomy and irrigation methods are described in Barbazetto, I A, et al. (2004). Accordingly, the hydroxylamine compound may be administered to the subject by infusion of the compound directly into the irrigating solution. This may be accomplished by equilibrating the irrigation solution with the hydroxylamine compound prior to placement in the vitreous cavity. Alternatively, the hydroxylamine compound may be injected into the irrigating solution once it has been placed in the vitreous cavity, and this may occur prior to or after closing the surgical incision. The optimal concentration of the hydroxylamine compound to be present in the irrigating solution will be empirically determined according to methods routine in the art.

As part of a post-vitrectomy follow-up regimen, the hydroxylamine compounds may be continually administered to the subject, at least until such time as the body can replenish the vitreous humor and restore the natural oxygen gradient. In the course of the post-vitrectomy follow-up regimen, the hydroxylamine compounds may be administered to the subject by direct injection into the vitreous cavity or by topical administration, for example, through an eye drop. Alternatively, the hydroxylamine compounds may be administered to the subject by both direct injection into the vitreous cavity and by topical administration. Other means to administer the hydroxylamine compounds inside the vitreous cavity may also be used, and such are detailed above.

The proper dosage, optimal number of times to administer the compound (daily, weekly, etc.), and length time in which the hydroxylamines must be administered to the subject as part of a post-vitrectomy follow-up regimen will be empirically determined by methods that are routine in the art, and may vary with the needs of individual subjects.

The present invention is not limited to the embodiments described and exemplified above, but is capable of variation and modification within the scope of the appended claims.

What is claimed:

1. A method for inhibiting the development of a vitrectomy-induced cataract comprising administering to the vitreous of a subject undergoing a vitrectomy a composition comprising an ophthalmologically acceptable carrier or diluent and at least one hydroxylamine compound of the following formula:

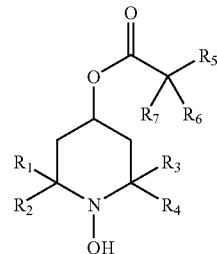

wherein $R_3$ and $R_4$ are, independently $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is $C_1$ to $C_6$ alkyl, alkenyl, alkynyl, or substituted alkyl or alkenyl;
$R_7$ is $C_1$ to $C_6$ alkyl, alkenyl, alkynyl, substituted alkyl, alkenyl, cycloalkyl, or heterocycle or where $R_6$ and $R_7$, or $R_5$, $R_6$ and $R_7$, taken together, form a carbocycle or heterocycle having from 3 to 7 atoms in the ring;
in a therapeutically sufficient amount to inhibit the development of a vitrectomy-induced cataract in the subject.

2. The method of claim 1, wherein the composition is administered before, during or after the vitrectomy is performed.

3. The method of claim 1 wherein the composition is administered to achieve in the vitreous tissue and fluids of the subject a concentration of about 0.1 µM to about 10 mM.

4. The method of claim 1 wherein the composition is administered to achieve in the vitreous tissue and fluids of the subject a concentration of about 1 µM to about 5 mM.

5. The method of claim 1 wherein the composition is administered to achieve in the vitreous tissue and fluids of the subject a concentration of about 10 µM to about 2.5 mM.

6. The method of claim 1 wherein the composition is administered to achieve in the vitreous tissue and fluids of the subject a concentration of about 50 µM to about 1 mM.

7. The method of claim 1 wherein the composition is administered to achieve in the eye tissue and fluids of the subject a concentration of about 1 µM to about 100 µM.

8. The method of claim 1 wherein the hydroxylamine compound is 1-hydroxy-4-cyclopropanecarbonyloxy-2,2,6,6-tetramethylpiperidine hydrochloride.

9. The method of claim 1 further comprising administering a reducing agent to the vitreous of the subject.

10. The method of claim 9, wherein the reducing agent is coadministered with the composition.

11. The method of claim 9, wherein the reducing agent is formulated as part of the composition.

12. The method of claim 9, wherein the reducing agent is administered separately from the composition.

13. The method of claim 9, wherein the reducing agent is a sulfhydryl compound.

14. The method of claim 13, wherein the reducing agent is mercaptopropionyl glycine, N-acetyl cysteine, β-mercaptoethylamine or glutathione.

15. The method of claim 1, wherein the composition is administered by injection.

16. The method of claim 1, wherein the composition is coadministered with irrigation solution during vitrectomy.

17. The method of claim 1, wherein the composition is formulated as part of the irrigation solution during vitrectomy.

18. The method of claim 1 further comprising administering to the vitreous of the subject after said vitrectomy a composition comprising an ophthalmologically acceptable carrier or diluent and at least one hydroxylamine compound of the following formula:

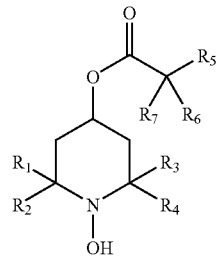

wherein $R_3$ and $R_4$ are, independently $C_1$ to $C_3$ alkyl; and where $R_1$ and $R_2$, taken together, or $R_3$ and $R_4$, taken together, or both may be cycloalkyl;

$R_5$ is H, OH, or $C_1$ to $C_6$ alkyl;

$R_6$ is $C_1$ to $C_6$ alkyl, alkenyl, alkynyl, or substituted alkyl or alkenyl;

$R_7$ is $C_1$ to $C_6$ alkyl, alkenyl, alkynyl, substituted alkyl, alkenyl, cycloalkyl, or heterocycle or where $R_6$ and $R_7$, or $R_5$, $R_6$ and $R_7$, taken together, form a carbocycle or heterocycle having from 3 to 7 atoms in the ring;

in a therapeutically sufficient amount to inhibit the development of a vitrectomy-induced cataract in the subject.

19. The method of claim 18, wherein the composition administered after the vitrectomy is performed to achieve in the vitreous tissue and fluids of the subject a hydroxylamine concentration of about 0.1 μM to about 10 mM.

20. The method of claim 18, wherein the composition administered after the vitrectomy is injected into the vitreous.

21. The method of claim 18, wherein said composition administered after said vitrectomy is an eyewash, eye drop or ophthalmic ointment.

22. The method of claim 18, wherein the composition administered after said vitrectomy is administered from a polymeric disc or wafer placed on the surface of the eye.

23. The method of claim 18 wherein the hydroxylamine compound is 1-hydroxy-4-cyclopropanecarbonyloxy-2,2,6,6-tetramethylpiperidine hydrochloride.

* * * * *